US011351553B2

(12) United States Patent
Lee et al.

(10) Patent No.: US 11,351,553 B2
(45) Date of Patent: Jun. 7, 2022

(54) HEATING MECHANISM FOR BIOCHEMICAL REACTION DEVICE

(71) Applicant: GENEREACH BIOTECHNOLOGY CORP., Taichung (TW)

(72) Inventors: Chun-Ming Lee, Taichung (TW); Ching-Ko Lin, Taichung (TW); Yun-Lung Tsai, Taichung (TW); Pei-Yu Lee, Taichung (TW); Chen Su, Taichung (TW); Hsiao-Fen Chang, Taichung (TW); Fu-Chun Li, Taichung (TW)

(73) Assignee: GENEREACH BIOTECHNOLOGY CORP., Taichung (TW)

( * ) Notice: Subject to any disclaimer, the term of this patent is extended or adjusted under 35 U.S.C. 154(b) by 413 days.

(21) Appl. No.: 16/628,526

(22) PCT Filed: Sep. 19, 2017

(86) PCT No.: PCT/CN2017/102233
§ 371 (c)(1),
(2) Date: Jan. 3, 2020

(87) PCT Pub. No.: WO2019/056168
PCT Pub. Date: Mar. 28, 2019

(65) Prior Publication Data
US 2020/0156078 A1     May 21, 2020

(51) Int. Cl.
*B01L 7/00*     (2006.01)
*B01L 9/00*     (2006.01)
*C12M 1/38*     (2006.01)

(52) U.S. Cl.
CPC ............ *B01L 7/52* (2013.01); *B01L 9/50* (2013.01); *C12M 1/38* (2013.01); *B01L 2300/1805* (2013.01)

(58) Field of Classification Search
CPC .......................................................... B01L 7/52
See application file for complete search history.

(56) References Cited

U.S. PATENT DOCUMENTS

| 6,558,947 B1 * | 5/2003 | Lund .................. B01L 7/54 435/303.1 |
| 8,563,907 B2 * | 10/2013 | Bushman ............... G21F 5/015 219/535 |

(Continued)

FOREIGN PATENT DOCUMENTS

| CN | 101735949 A | 6/2010 |
| CN | 104293662 A | 1/2015 |
| WO | 2016/145573 A1 | 9/2016 |

*Primary Examiner* — Jonathan M Hurst
(74) *Attorney, Agent, or Firm* — Rabin & Berdo, P.C.

(57) ABSTRACT

Provided is a heating mechanism for a biochemical reaction device, including: a heat-conducting body including: at least one accommodating groove each including a chamber and an opening communicating with the chamber; a clamping hole, in communication with the opening and for inserting a reaction tube; and at least one heat-conducting block, movably disposed in the chamber and having one end connected with an elastic element and another opposite end provided with an abutting portion, the elastic element enabling the abutting portion of the heat-conducting block to protrude from the opening and locate in the clamping hole; and a temperature control element connected to the heat-conducting body for heating and regulating a temperature of the heat-conducting block. The heat-conducting blocks of the heating mechanism can be in direct and assured contact with the reaction tube for conducting heat, so that the solution in the reaction tube can easily and assuredly reach a preset temperature, thereby achieving a consistent reaction condition and increasing the accuracy of the reaction result.

10 Claims, 11 Drawing Sheets

(56) References Cited

U.S. PATENT DOCUMENTS

| | | | |
|---|---|---|---|
| 2005/0003518 A1 | 1/2005 | Aviram et al. | |
| 2005/0009070 A1* | 1/2005 | Arciniegas | B01L 9/06 435/287.2 |
| 2008/0254532 A1* | 10/2008 | Chang | B01L 3/505 435/288.7 |
| 2011/0207632 A1 | 8/2011 | Belgrader et al. | |
| 2016/0242237 A1* | 8/2016 | Su | H05B 3/42 |
| 2018/0360023 A1* | 12/2018 | McPherson | B01L 7/00 |
| 2018/0361387 A1* | 12/2018 | Knippschild | B01L 7/52 |

* cited by examiner

HEATING MECHANISM FOR BIOCHEMICAL REACTION DEVICE

BACKGROUND OF THE INVENTION

1. Field of the Invention

The present invention relates generally to a heating device, and more particularly to a heating mechanism for heating or regulating the temperature of a reaction tube in a biochemical reaction device.

2. The Prior Arts

Biochemical reaction devices, such as polymerase chain reaction (PCR) devices, must undergo loops of three reaction steps, including denaturation, annealing, and extension, when performing nucleic acid amplification reactions. Each reaction step has a preset optimal reaction temperature. For example, the denaturation reaction is generally set between about 90 and 95° C., the annealing reaction is set between about 35 to 65° C. depending on the different primers, and the extension reaction is set at a temperature of about 72° C. suitable for the polymerase reaction. The aforementioned reaction temperatures are closely correlated to the results of nucleic acid amplification, especially in the annealing reaction stage. If it is used to detect a target nucleic acid, the positive or negative determination is further affected by the reaction conditions. Therefore, accurate control of the reaction temperature is one of the important requirements of the device.

In regard to the use of the heating mechanism in the polymerase chain reaction device, the reaction tubes containing the reaction solution are respectively placed into a heating module provided with a plurality of holes, thereby achieving the purpose of controlling the temperature of the reaction tubes through a heat conduction by the contact between an inner wall of the heating module and the reaction tubes. However, since the numerous types and specifications of the reaction tube will cause uneven or insufficient contact between the outer wall of the reaction tube and the hole of the heating module, this may result in the uneven temperature of the solution in the reaction tube or the solution may fail to reach the preset temperature, thereby lowering efficiency of the reaction or yield of the amplified product. When the reaction tubes are used to detect a specific target nucleic acid sequence, the accuracy of the detection result is also affected.

In order to solve the above problem, mineral oil may be added to the hole to fill the gap between the reaction tube and the hole to improve heat transfer efficiency. However, the addition of mineral oil may easily cause sample contamination and cause mechanical cleaning and maintenance difficulties. More importantly, the mineral oil will also absorb and dissipate heat. After adding different volumes of mineral oil to the holes, there is also often a difference between the actual temperature and the preset temperature among the holes or even in the whole heating module. In addition, the heating module is bulky and thus requires a longer time to heat and dissipate heat, and therefore the required overall reaction time increases.

SUMMARY OF THE INVENTION

The present invention provides a heating mechanism for a biochemical reaction device capable of conveniently placing a reaction container to be heated therein and capable of easily limiting the reaction container in a position. According to the heating mechanism of the present invention, the reaction container can be easily held and fixed in the heating mechanism by applying a thrust thereto but without deliberately adjusting the placement position of the reaction container, and then can be heated by heat conduction due to the clamping by the heat-conducting blocks thereon.

The present invention also provides a heating mechanism capable of precisely regulating the temperature of a biochemical reaction. According to the heating mechanism of the present invention, the heat-conducting blocks can be in close and direct contact with the reaction container for heat conduction, so that the solution in the reaction container can assuredly reach the preset temperature. As such, the heating conditions of the respective reaction containers are consistent with each other, so that the reaction can be more efficiently performed with fast heat transfer, and the reproducibility and accuracy of the reaction result can also be improved.

The present invention also provides a heating mechanism that can reduce the volume of a biochemical reaction device. According to the small and compact heating mechanism of the present invention, the same objective of the heat conduction can be achieved, but the required volume and space for the overall device can be reduced. Also, because of the compact size, it is more convenient in maintenance and replacement.

The present invention also provides a heating mechanism for a biochemical reaction device capable of shortening the reaction time. According to the small and compact heating mechanism of the present invention, the heating time and the heat dissipation time can be shortened, so that the time required for the overall reaction is greatly shortened, and thus the reaction efficiency can be improved.

The present invention provides a heating mechanism for a biochemical reaction device, comprising: a heat-conducting body, the heat-conducting body comprising: at least one accommodating groove each comprising a chamber and an opening communicating with the chamber; a clamping hole, in communication with the opening and for insertion of a reaction tube; and at least one heat-conducting block, movably disposed in the chamber and having one end connected with an elastic element and another opposite end provided with an abutting portion, the elastic element enabling the abutting portion of the heat-conducting block to protrude from the opening and locate in the clamping hole; and a temperature control element, the temperature control element being connected to the heat-conducting body for heating and regulating a temperature of the heat-conducting block.

In an embodiment of the present invention, the heating mechanism of the biochemical reaction device further comprises a reaction container, and the reaction container may further be provided with a heat-conducting element. When the reaction container is inserted into the heat-conducting body through the clamping hole, the reaction container is pressed by the abutting portion of the heat-conducting block reaction hole so that the reaction container is clamped therein and the heat-conducting element is in contact with the heat-conducting block to conduct heat energy.

In the heating mechanism of the biochemical reaction device according to an embodiment of the present invention, the accommodating groove is provided in plurality, and the openings provided in the accommodating grooves are distributed in a circumferential range of the clamping hole by about 270°, preferably a circumferential range of the clamping hole by about 180°, for one-sided heating the reaction tube. The accommodating grooves and the openings thereof may also be equally spaced apart in a circumference of the clamping hole to uniformly heat an outer edge of the reaction tube.

In the heating mechanism of the biochemical reaction device according to an embodiment of the present invention, the temperature control element is laid on and connected to a surface of the heat-conducting body, and the temperature control element is provided with a first through-hole, the first through-hole is in communication with the clamping hole.

In the heating mechanism of the biochemical reaction device according to an embodiment of the present invention, the abutting portion of the heat-conducting block is spherical, and thus the heat-conducting block may be a shape of an ellipsoid, a sphere, a semi-ellipsoid or a hemisphere.

In an embodiment of the present invention, the abutting portion has a circular arc shape. In another embodiment of the present invention, an end of the abutting portion provided for the insertion of the reaction tube has a sloped surface.

In the heating mechanism of the biochemical reaction device according to an embodiment of the present invention, the heat-conducting body is further provided with a recessed groove on the accommodating groove, and a limiting member is disposed in the recessed groove. The limiting member is provided with a second through-hole, and the second through-hole is in communication with a first through-hole of the temperature control element, and the clamping hole.

Since the reaction container for biochemical reaction can be easily placed in the clamping hole of the heat-conducting body of the present invention and clamped by the heat-conducting block, on the one hand, the reaction container can be fixed, and on the other hand, the direct contact between the reaction container and each heat-conducting block can be ensured. This avoids the disadvantage of the failure of contact between the outer edge of the reaction container and the heat-conducting block due to an offset placement of the reaction container. Therefore, not only the portion where the reaction container is in contact with the heat-conducting block can be heated uniformly, but also the consistency of the conditions of the heating reaction each time can be ensured, so that the biochemical reaction is reproducible and the reaction result is more accurate. In addition, since the reaction container is disposed in an insertion and clamping manner in the heating mechanism of the present invention, it is not necessary to provide a heating element or a heating module with a shape corresponding to that of the reaction container. Therefore, the reaction container or the heating device can be manufactured with a more widely allowable tolerance range, thereby reducing the manufacturing cost. On the other hand, because of the assured contact between the reaction container and the heat-conducting block, the heat energy can be quickly and precisely transferred to the reaction container. Therefore, the solution in the reaction tube can react accurately at the preset temperature, thereby further improving the reaction efficiency and the reaction accuracy.

The embodiments of the present invention are further described below, and the following examples are set forth to illustrate the present invention, and are not intended to limit the scope of the present invention. Those skilled in the art can make various changes and modifications without departing from the spirit and scope of the present invention. Therefore, the protection scope of the present invention shall be defined by the appended claims.

DETAILED DESCRIPTION OF THE PREFERRED EMBODIMENT

Figure 1:
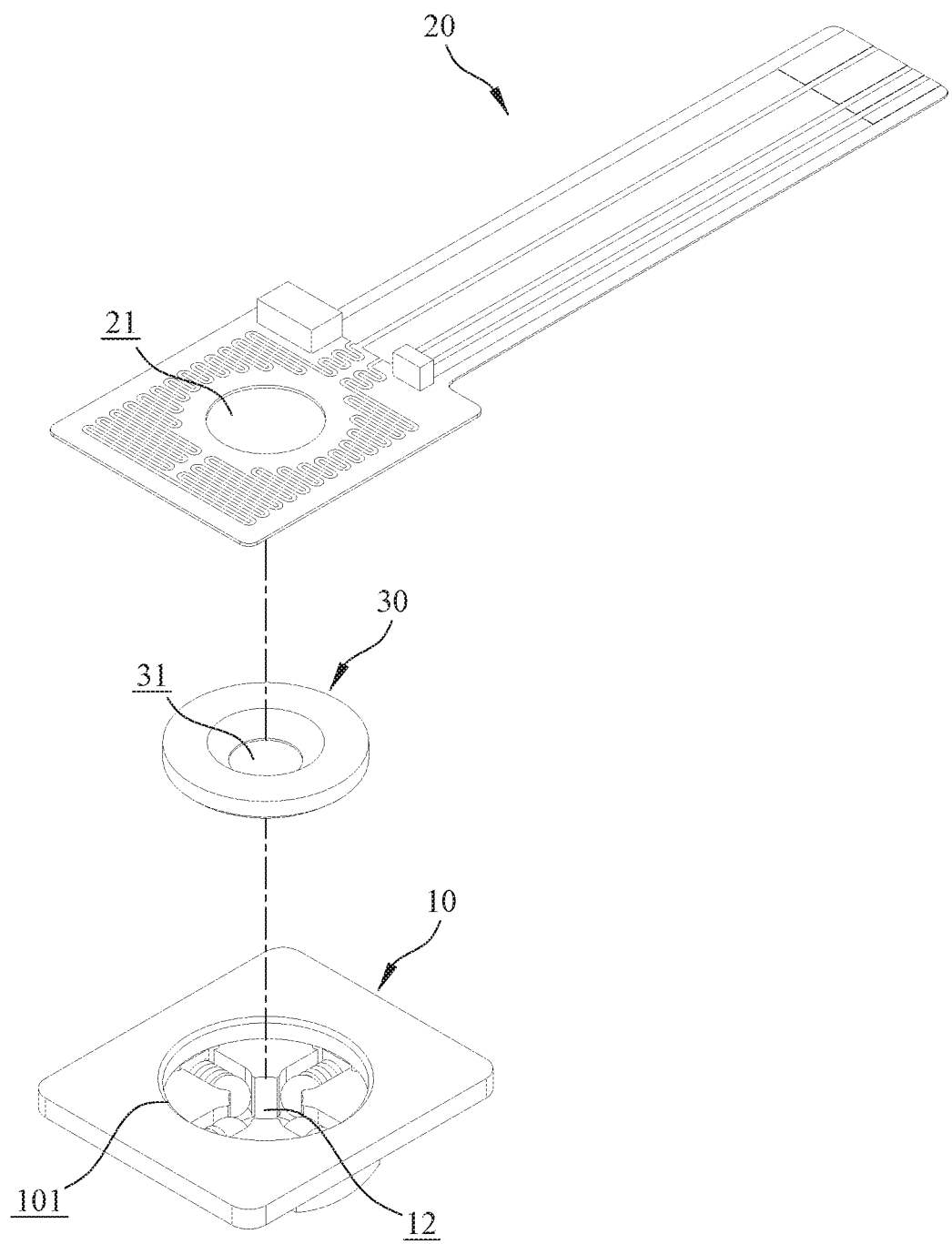
FIG. 1 is an exploded schematic view of a heating mechanism according to an embodiment of the present invention.

Referring to FIG. 1, FIG. 1 is an exploded schematic view of a heating mechanism according to an embodiment of the present invention. The heating mechanism of the biochemical reaction device of the present invention comprises a heat-conducting body 10 and a temperature control element 20, and the temperature control element 20 is connected to the heat-conducting body 10 for heat conducting and regulating the temperature change of the heat-conducting body 10. For the convenience of assembling, the heat-conducting body 10 may be formed with a recessed groove 101, and a limiting member 30 is disposed therein, so that related elements of the heat-conducting body 10 are limited therein. A clamping hole 12 provided in the heat-conducting body 10, a first through-hole 21 provided in the temperature control element 20 and a second through-hole 31 provided in the limiting member 30 are in communication with one another, so that a reaction container 40 (see FIG. 5) is clamped herein after inserting. The shape, length and outer diameter of the reaction container may be, but not limited to, designed according to the volume of the reaction solution and the shape of the corresponding heating mechanism. Optionally, the reaction container may be a tubular container, such as the reaction tube 40 of the embodiment. The tubular container may be, but not limited to, a circular tube or a polygonal tube.

Figure 2:
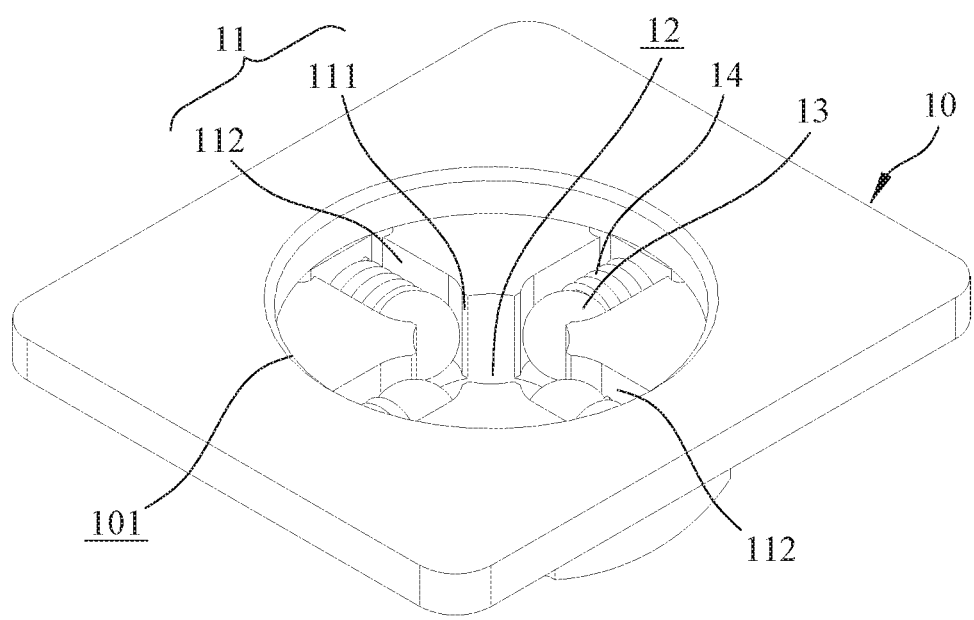
FIG. 2 is a perspective schematic view of a heat-conducting body in the heating mechanism according to an embodiment of the present invention.

Referring to FIG. 2, FIG. 2 is a schematic view of a heat-conducting body in the heating mechanism according to an embodiment of the present invention. The structural shape of the heat-conducting body 10 is not particularly limited, and may be adjusted according to the requirements of the device, the size of the reaction tube, and the temperature control element. The clamping hole 12 of the heat-conducting body 10 is provided for insertion of the reaction tube 40. The clamping hole 12 may be a through-hole or a blind hole, as long as the reaction tube 40 can enter and be clamped therein. In addition, at least one accommodating groove 11 is disposed in the heat-conducting body 10, and each accommodating groove 11 includes a chamber 112 in which a heat-conducting block 13 is disposed, and the chamber 112 is extended to communicate with an opening 111, and the opening 111 is connected to the clamping hole 12.

Figure 3:
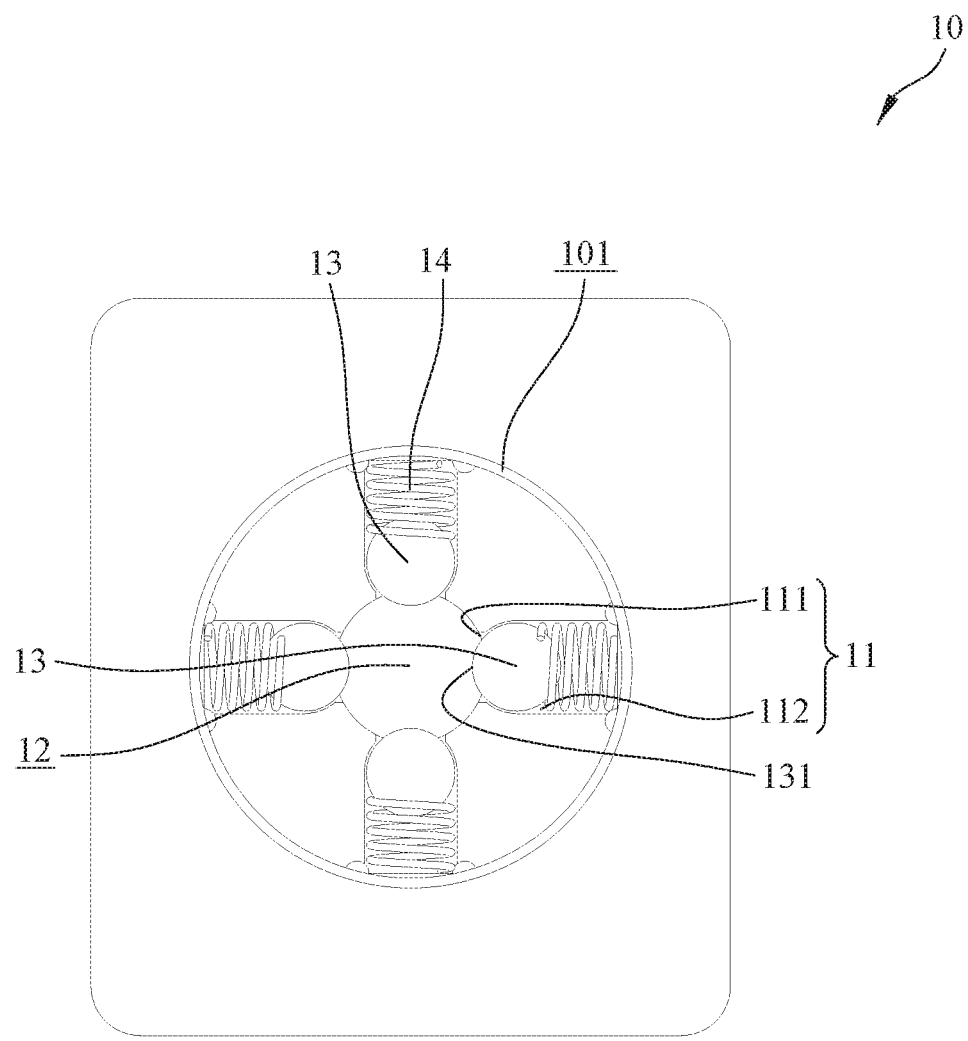
FIG. 3 is a top view of the heat-conducting body in the heating mechanism according to an embodiment of the present invention.

Referring to FIG. 2 and FIG. 3, FIG. 3 is a top view of the heat-conducting body in the heating mechanism according to an embodiment of the present invention. The heat-conducting block 13 is disposed in the chamber 112 in a movable manner and one end of the heat-conducting block 13 is connected to an elastic member 14. The heat-conducting block 13 is pushed by an elastic force of the elastic member 14 towards against the opening 111. As such, an abutting portion 131 of the heat-conducting block 13 is exposed to protrude from the opening 111 and is located in the clamping hole 12. Therefore, the opening 111 is sized to expose the abutting portion 131, but the heat-conducting block 13 as a whole is still located in the chamber 112.

Figure 4:
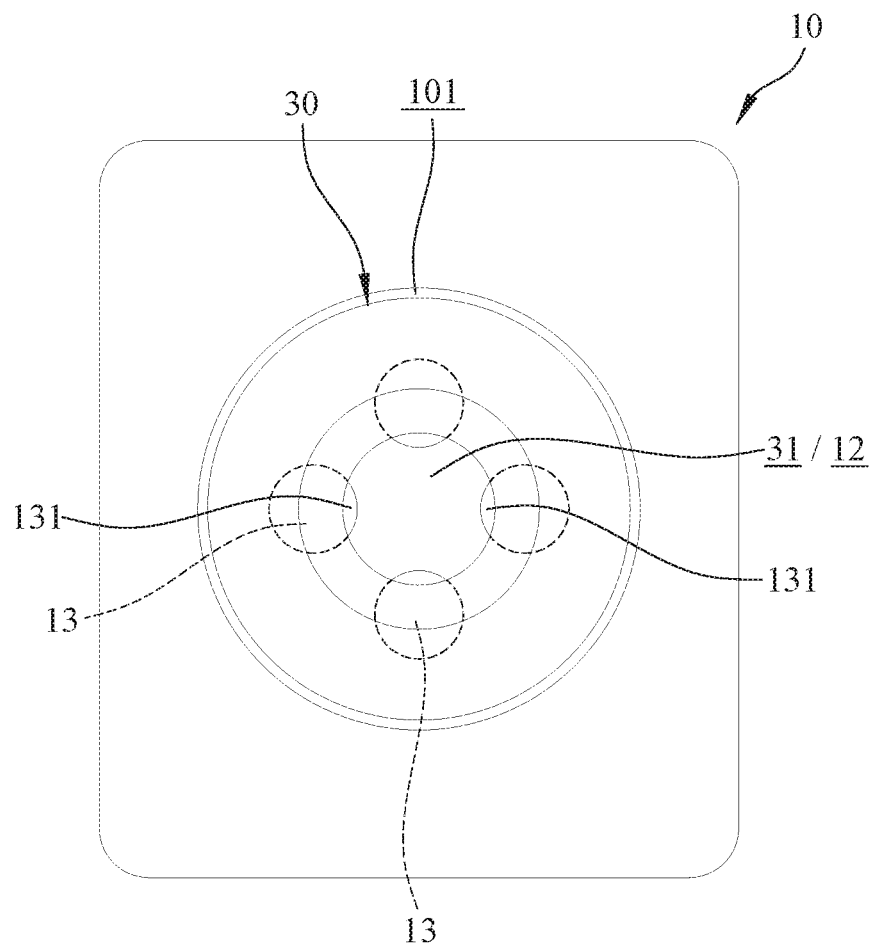
FIG. 4 is a schematic view of the heat-conducting body after assembling a limiting member in the heating mechanism according to an embodiment of the present invention.

Referring to FIG. 4, FIG. 4 is a schematic view of the heat-conducting body after assembling a limiting member in the heating mechanism according to an embodiment of the present invention. Furthermore, for the convenience of assembling, the limiting member 30 can be installed in the recessed groove 101 of the heat-conducting body 10, and thus the heat-conducting block 13 and the like can be limited in the heat-conducting body 10. Therefore, the structure of the limiting member 30 is not particularly limited or does not necessarily have to be installed. After the limiting member 30 is installed, the second through-hole 31 must also be provided to communicate with the clamping hole 12, so that the reaction tube 40 can pass and then be placed therein, and the abutting portion 131 of the heat-conducting block 13 is still exposed in the clamping hole 12, so that the reaction tube 40 can be in contact with the abutting portion 131 when inserted into the clamping hole 12, and thus be clamped by the action of the elastic force.

Figure 5:
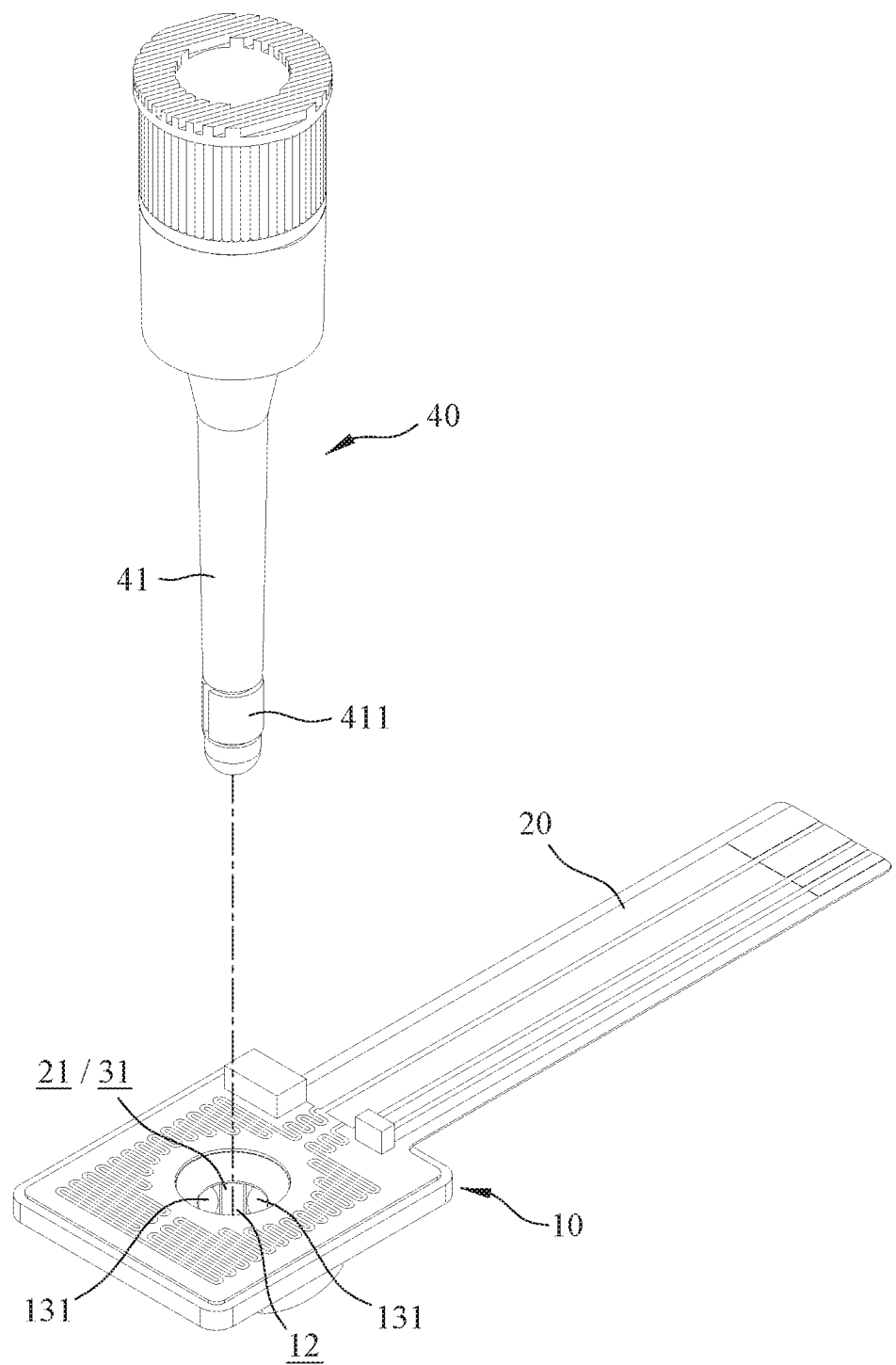
FIG. 5 is a schematic view of the heating mechanism ready for insertion of a reaction tube therein according to an embodiment of the present invention.
Figure 6A:
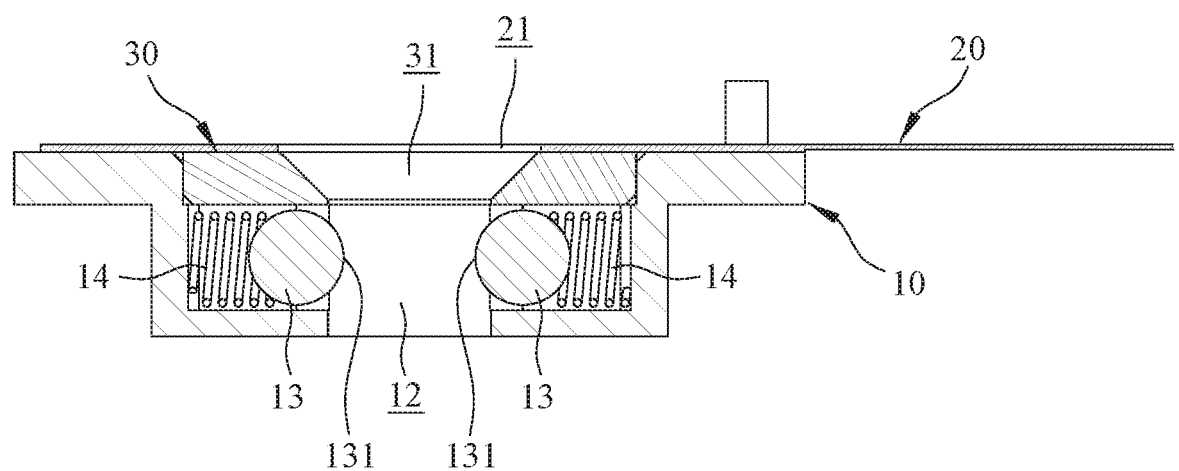
FIG. 6A is a cross-sectional view of the heating mechanism without inserting the reaction tube according to an embodiment of the present invention.
Figure 6B:
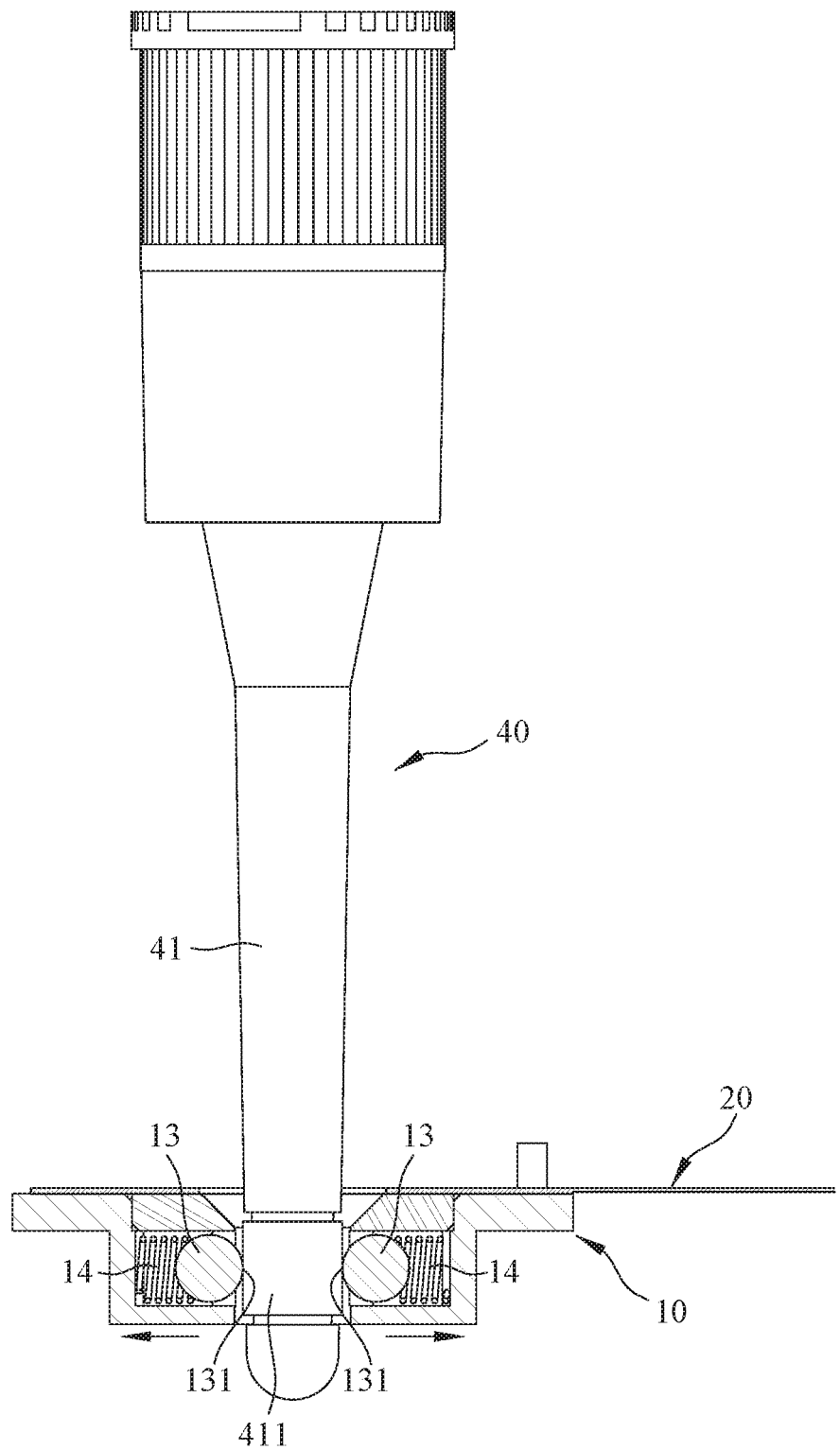
FIG. 6B is a cross-sectional view of the heating mechanism after inserting the reaction tube according to an embodiment of the present invention.

Referring to FIG. 5, FIG. 6A and FIG. 6B, FIG. 5 is a schematic view of the heating mechanism ready for insertion of the reaction tube according to an embodiment of the present invention; FIG. 6A is a cross-sectional view of the heating mechanism without inserting the reaction tube according to an embodiment of the present invention; and FIG. 6B is a cross-sectional view of the heating mechanism after inserting the reaction tube according to an embodiment of the present invention. The temperature control element 20 is provided to regulate the temperature of the heat-conducting block 13, and the arrangement position and manner thereof are not particularly restricted, and may be provided, but not limited to, on a part or all of an upper surface of the heat-conductive body 10 (the surface facing the insertion direction of the reaction tube 40), a part or all of side surfaces of the heat-conductive body 10, or a part or all of a lower surface of the heat-conductive body 10 (the surface opposite to the upper surface). In the present embodiment, the temperature control element 20 is laid in shape matching on and connected to the upper surface of the heat-conducting body 10, and then the heat energy generated by the heating wire (not shown) disposed thereon is first transferred to the heat-conducting body 10, and then transferred to the heat-conducting block 13 for heating. In performing the heating, the reaction tube 40 passes the first through-hole 21 of the temperature control unit 20 and the second through-hole 31 of the limiting member 30 and enters the clamping hole 12 of the heat-conducting body 10. When the reaction tube 40 enters the clamping hole 12, since the abutting portions 131 of the heat-conducting blocks 13 protrude therein, and the inner diameter defined by the abutting portions 131 is smaller than the outer diameter of the tubular body 41 of the reaction tube 40, the reaction tube 40 will experience a hindrance of the clamping, and after a small force is applied, the outer wall of the front end of the tubular body 41 can push the abutting portion 131 of the heat-conducting block 13 towards the inside of the chamber 112 to overcome the action of the elastic force by an oblique component force through a surface of the heat-conducting block 13. At this moment, the front end of the tubular body 41 can overcome the hindrance of the abutting portion 131 of the heat-conducting block 13 to pass through therebetween. After that, the tubular body 41 is clamped between the abutting portions 131/the heat-conducting blocks 13. Thereafter, the subsequent reactions can be performed.

In order to further make the heat transfer more rapid and uniform, the tubular body 41 of the reaction tube 40 may be provided with a heat-conducting element 411. The heat conducting element 411 may be disposed in a region configuration, a single side configuration or a circumferential configuration on the tubular body 41 according to the arrangement of the heat-conducting blocks 13. In the embodiment, the heat-conducting element 411 is disposed in a circumferential configuration. Furthermore, the material of the heat-conducting element 411 is not particularly limited, but preferably has a higher heat transfer coefficient. It should be noted that in the case where the reaction tube 40 is provided with the heat-conducting element 411, after the reaction tube 40 is inserted, the position of the heat-conducting element 411 should be corresponding to the position of the abutting portion 131, so that a heat can be transferred therebetween.

It should be noted that the number and position of the accommodating grooves 11 are not particularly limited. It can be with only a single accommodating groove 11 and only an opening 111. Therefore, when the reaction tube 40 is inserted and clamped by the heat-conducting block 13, one-sided heating is performed. This heating way can be applied to, for example, a device for a convectional PCR. If a plurality of accommodating grooves 11 are provided, the accommodating grooves 11 may be disposed in a circumferential range of the arranging hole 12 by about 270 degrees to allow the openings 111 to face an outer edge of one side of the reaction tube 40 so that the plurality of heat-conducting blocks 13 performs one-sided heating. Alternatively, the accommodating grooves 11/openings 111 may be equally spaced apart in the circumference of the clamping hole 12 to perform heating evenly on the circumference of the outer edge of the reaction tube 40. This can also be applied to a general PCR reaction device.

Figure 7:
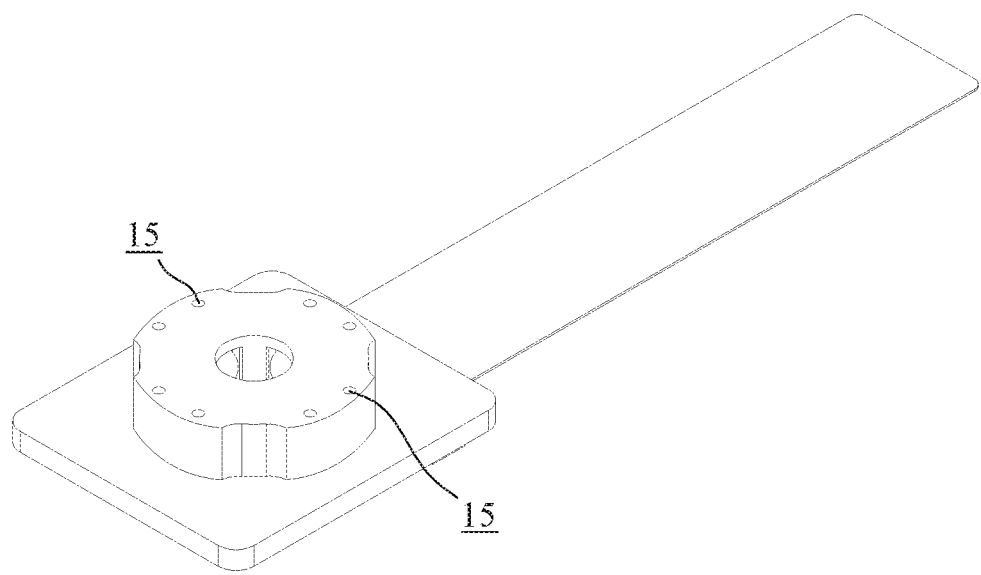
FIG. 7 is a schematic view of a bottom portion of the heat-conducting body in the heating mechanism according to an embodiment of the present invention.

Referring to FIG. 7, FIG. 7 is a schematic view of a bottom portion of the heat-conducting body in the heating mechanism according to an embodiment of the present invention. In order to allow the heat-conducting body 10 to dissipate heat rapidly after heating, a heat dissipation hole 15 communicating with the accommodating groove 11 may be provided. The position of the heat dissipation hole 15 is not particularly limited. In the present embodiment, the heat dissipation hole 15 is disposed at a bottom of the heat-conducting body 10, that is, a bottom of the accommodating groove 11, and the number of the heat dissipation holes may be determined, but not limited, according to the size of the structure or the range of the reaction temperature.

Figure 8A:
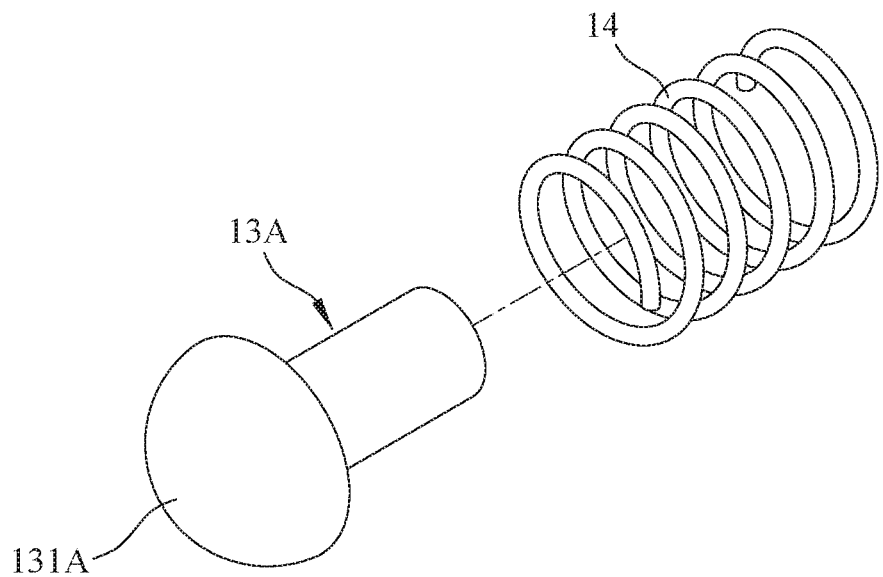
FIG. 8A is a schematic view of an abutting portion of a heat-conducting block in the heating mechanism according to an embodiment of the present invention.
Figure 8B:
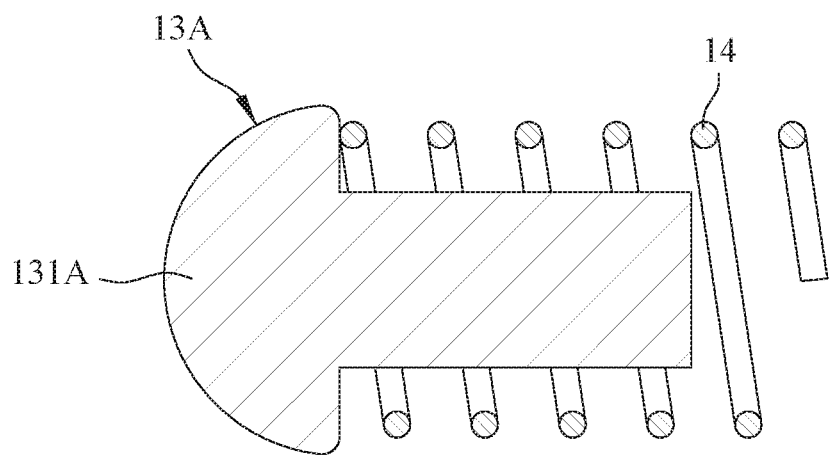
FIG. 8B is a cross-sectional view of the heat-conducting block of FIG. 8A.
Figure 8C:
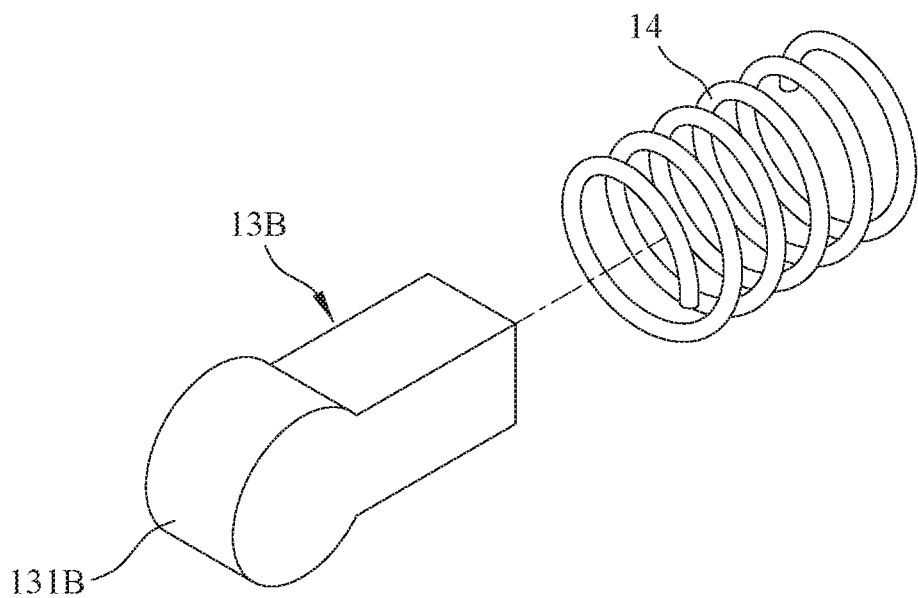
FIG. 8C is a schematic view of an abutting portion of a heat-conducting block in the heating mechanism according to another embodiment of the present invention.
Figure 8D:
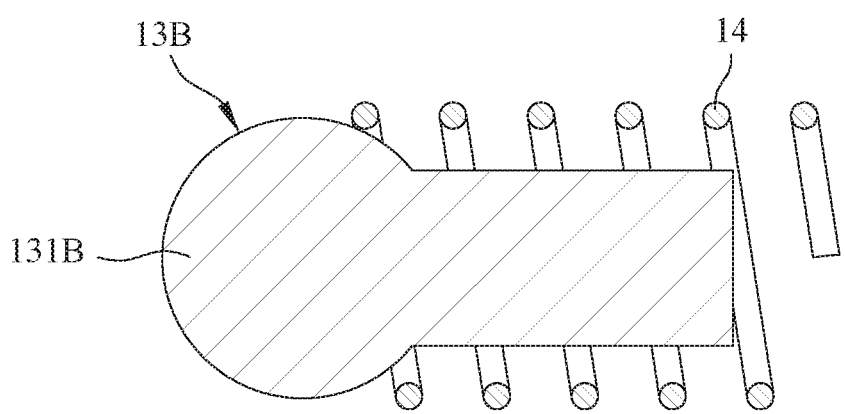
FIG. 8D is a cross-sectional view of the heat-conducting block of FIG. 8C.
Figure 8E:
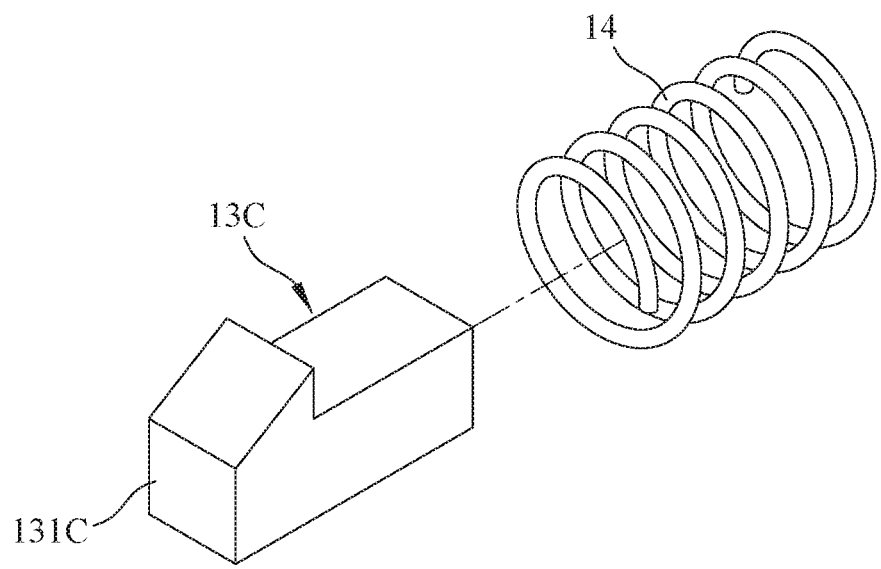
FIG. 8E is a schematic view of the abutting portion of a heat-conducting block in the heating mechanism according to another embodiment of the present invention.
Figure 8F:
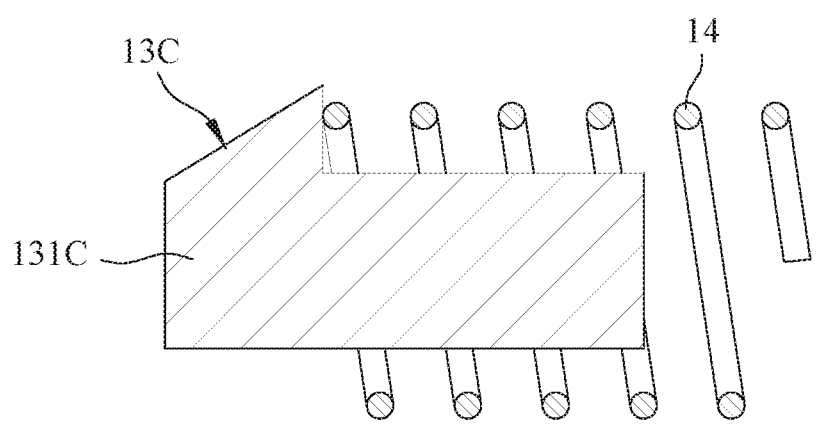
FIG. 8F is a cross-sectional view of the heat-conducting block of FIG. 8E.

Refer to FIG. 8A-FIG. 8F, which show various embodiments of the abutting portion of the heat-conducting block. The purpose of the heat-conducting block 13 is to clamp the reaction tube 40 and to transfer heat. Therefore, the structure thereof is not particularly limited, and it would be sufficient that only the front end of the tubular body 41 can be smoothly passed through the abutting portions 131 and clamped between the abutting portions 131/the heat-conducting blocks 13 as the reaction tube 40 is inserted. Therefore, the abutting portion 131 may have various configurations, which can be a structure of spherical surface. In this case, the heat-conducting block 13 is a spherical, such as shown in FIG. 2, or an ellipsoidal, semi-ellipsoidal or hemispherical structure (not shown) and further directly connected to the elastic member 14. Furthermore, a heat-conducting block 13A shown in FIG. 8A and FIG. 8B may have an abutting portion 131A with a hemispherical/semi-ellipsoidal structure, or a heat-conducting block 13B as shown in FIG. 8C and FIG. 8D may have an abutting portion 131B with an arc-shaped structure, or a heat-conducting block 13C shown in FIG. 8E and FIG. 8F may have an abutting portion 131C with a sloped surface structure for the insertion of the reaction tube. The heat-conducting block is sleeve-connected to the elastic member 14 through a columnar extension structure. Herein, the elastic member 14 can be, but not limited to, a spring.

Since the heat-conducting body 10 of the present invention is compact and small, and the reaction tube can be directly clamped, the accuracy and speed of heat transfer can be greatly improved. Therefore, reaction can be performed under the preset temperature in the reaction tube, and thus both the reaction efficiency and the product yield can be significantly improved.

What is claimed is:

1. A heating mechanism for a biochemical reaction device, comprising:
   a heat-conducting body, the heat-conducting body comprising:
      at least one accommodating groove each comprising a chamber and an opening communicating with the chamber;
      a clamping hole, in communication with the opening and for insertion of a reaction tube; and
      at least one heat-conducting block, movably disposed in the chamber and having one end connected to an elastic element and another opposite end provided with an abutting portion, the elastic element enabling the abutting portion of the heat-conducting block to protrude from the opening and locate in the clamping hole; and
   a temperature control element, the temperature control element being connected to the heat-conducting body for heating and regulating a temperature of the heat-conducting block.

2. The heating mechanism for the biochemical reaction device according to claim 1, wherein the accommodating groove is provided in plurality, and the openings provided in the accommodating grooves are distributed in a circumferential range of the clamping hole by about 270°.

3. The heating mechanism for the biochemical reaction device according to claim 1, wherein the accommodating groove is provided in plurality, and the openings provided in the accommodating grooves are evenly distributed in a circumference of the clamping hole.

4. The heating mechanism for the biochemical reaction device according to claim 1, wherein the temperature control element is laid on and connected to an upper surface, side surfaces or a lower surface of the heat-conducting body.

5. The heating mechanism for the biochemical reaction device according to claim 1, wherein the abutting portion of the heat-conducting block is spherical.

6. The heating mechanism for the biochemical reaction device according to claim 5, wherein the heat-conducting block is a sphere.

7. The heating mechanism for the biochemical reaction device according to claim 1, wherein the abutting portion of the heat-conducting block is arc-shaped.

8. The heating mechanism for the biochemical reaction device according to claim 1, wherein an end of the abutting portion of the heat-conducting block provided for the insertion of the reaction tube has a sloped surface.

9. The heating mechanism for the biochemical reaction device according to claim 1, wherein the heat-conducting body is further provided with a recessed groove on the accommodating groove, and a limiting member is disposed in the recessed groove, the limiting member is provided with a second through-hole, and the second through-hole is in communication with a first through-hole of the temperature control element, and the clamping hole.

10. The heating mechanism for the biochemical reaction device according to claim 1, further comprising a reaction container, and the reaction container being provided with a heat-conducting element, wherein when the reaction container is inserted into the heat-conducting body through the clamping hole, the reaction container is pressed by the abutting portion of the heat-conducting block so that the reaction container is clamped therein and the heat-conducting element is in contact with the heat-conducting block to conduct heat energy.

* * * * *